United States Patent [19]

Rhodes

[11] Patent Number: 5,145,683
[45] Date of Patent: Sep. 8, 1992

[54] NIFEDIPINE-CONTAINING PHARMACEUTICAL COMPOSITIONS AND PROCESS FOR THE PREPARATION THEREOF

[75] Inventor: Alan Rhodes, Ely, United Kingdom

[73] Assignee: Ethical Pharmaceuticals, Ltd., Cambridgeshire, United Kingdom

[21] Appl. No.: 472,659

[22] Filed: Jan. 30, 1990

[30] Foreign Application Priority Data

Feb. 14, 1989 [GB] United Kingdom ................ 8903328

[51] Int. Cl.$^5$ .................. A61K 9/14; A61K 9/22; A61K 9/52
[52] U.S. Cl. .................. 424/451; 424/462; 424/468; 424/497; 514/299
[58] Field of Search .................. 424/462, 468, 497; 514/299

[56] References Cited

U.S. PATENT DOCUMENTS

| | | | |
|---|---|---|---|
| 4,412,986 | 11/1983 | Kawata et al. | 424/80 |
| 4,562,069 | 12/1985 | Hegasy et al. | 424/462 |
| 4,765,990 | 8/1988 | Sugimoto et al. | 424/494 |
| 4,840,799 | 6/1989 | Appelgren et al. | 424/497 |
| 4,880,623 | 11/1989 | Piergiorgio et al. | 424/468 |

FOREIGN PATENT DOCUMENTS

| | | |
|---|---|---|
| 1180277 | 1/1985 | Canada. |
| 0220760 | 5/1987 | European Pat. Off. . |
| 1579818 | 11/1980 | United Kingdom . |
| 2139892 | 11/1984 | United Kingdom . |
| WO86/01717 | 3/1986 | World Int. Prop. O. . |

OTHER PUBLICATIONS

Sugimoto et al., *Drug Development in Industrial Pharmacy*, 6(2) pp. 137-160 (1980).
Chem. Pharm. Bull., vol. 30, No. 12, I. Sugimoto et al, "Stability and bioavailability of Nifedipine in fine granules", 1982, pp. 4479-4488.
Chemical Abstracts, vol. 96, No. 14, I. Sugimoto et al, "Formulation study for increasing bioavailability of nifedipine" 1982, p. 382.

*Primary Examiner*—Thurman K. Page
*Assistant Examiner*—Amy Hulina
*Attorney, Agent, or Firm*—Bacon & Thomas

[57] ABSTRACT

A pharmaceutical composition which comprises particles of a finely divided pharmaceutically acceptable water soluble diluent coated with microcrystalline particles of nifedipine, the majority of which have a particle size of 100 micrometers or less in the presence of polyvinyl-pyrrolidone, the polyvinylpyrrolidone being present in an amount of from 10 to 90% by weight based on the weight of the nifedipine. The incorporation of polyvinylpyrrolidone in an amount of less than the amount of nifedipine significantly slows the dissolution of nifedipine from the finished solid dosage form.

18 Claims, 3 Drawing Sheets

NIFEDIPINE-CONTAINING PHARMACEUTICAL COMPOSITIONS AND PROCESS FOR THE PREPARATION THEREOF

The present invention relates to nifedipine-containing pharmaceutical compositions and to a process for the preparation thereof. In particular the present invention relates to a slow release formulation containing nifedipine and to a process for the preparation thereof.

The drug nifedipine is currently used in the form of quickly available and slowly available pharmaceutical dosage forms for the treatment, respectively, of acute angina and chronic hypertension. It would appear that, for the acute treatment of angina, it is desirable quickly to attain plasma nifedipine concentrations of about 100 ng/ml or greater and this requirement is currently served by a preparation consisting of a solution of nifedipine in low molecular weight polyethylene glycol contained within soft gelatin capsules. For the treatment of hypertension it would appear that it is more desirable to maintain plasma nifedipine concentrations within a therapeutic window of about 20-80 ng/ml, and slow release preparations of the substance are available for this purpose.

The reason for the two significantly different types of formulation being necessary is that nifedipine per se is very poorly soluble in water. This has led to a somewhat strange situation in the patent literature where patent specifications on controlled release system of nifedipine describe means of actually enhancing, rather than suppressing, the solubility of nifedipine.

Thus, in European Patent No. 0047899 (corresponding to Canadian Patent No. 1180277) control of the dissolution of nifedipine is achieved by processing the material to a large specific surface area of 0.5 to 6 $m^2/g$. The specification discloses the production of such nifedipine crystals by grinding and screening but not by any other means.

Similarly, in PCT/EP85/00481 the control of nifedipine dissolution is acheived by limiting its specific surface area to 0.1 to 0.4 $m^2/g$ and coating the nifedipine crystals, in admixture with an equal quantity of a filler, onto inert spheroids by means of suitable binders.

Further enhancement of the dissolution of nifedipine is afforded by processing the material to form a solution adsorbed onto a solid base (as in British Patent No. 1,456,618), or to form a solid solution (also known as a co-precipitate) with high molecular weight polyethylene glycol (European Patent Application No. 0220760) or an ester or ether of polyethylene glycol (European Patent Application No. 0249587) or with other selected materials, including polyvinyl pyrrolidone (British Patent No. 1,579,818).

This ability of polyvinylpyrrolidone to enhance the solubility characteristics of certain materials by forming coprecipitates with them is now fairly well documented. It is also generally accepted that in order to form such coprecipitates the amount of polyvinylpyrrolidone used must be in excess of the amount of active material. In fact the work of Sugimoto et al. (Drug Dev. Ind. Pharm. 1980. 6, 139-160) specifically concerning coprecipitates between nifedipine and polyvinylpyrrolidone found that the content of polyvinylpyrrolidone in the coprecipitate should be at least 75% for homogeneity.

In view of the above work on polyvinylpyrrolidone it was therefore found surprising that in the current invention polyvinylpyrrolidone in an amount less than the amount of nifedipine actually significantly slows the dissolution of nifedipine from the finished solid dosage form.

Accordingly, the present invention provides a pharmaceutical composition which comprises particles of a finely divided pharmaceutically acceptable water soluble diluent coated with microcrystalline particles of nifedipine, the majority of which have a particle size of 100 micrometers or less, in the presence of polyvinypyrrolidone, the polyvinylpyrrolidone being present in an amount of from 10 to 90% by weight based on the weight of the nifedipine.

Figure 1:
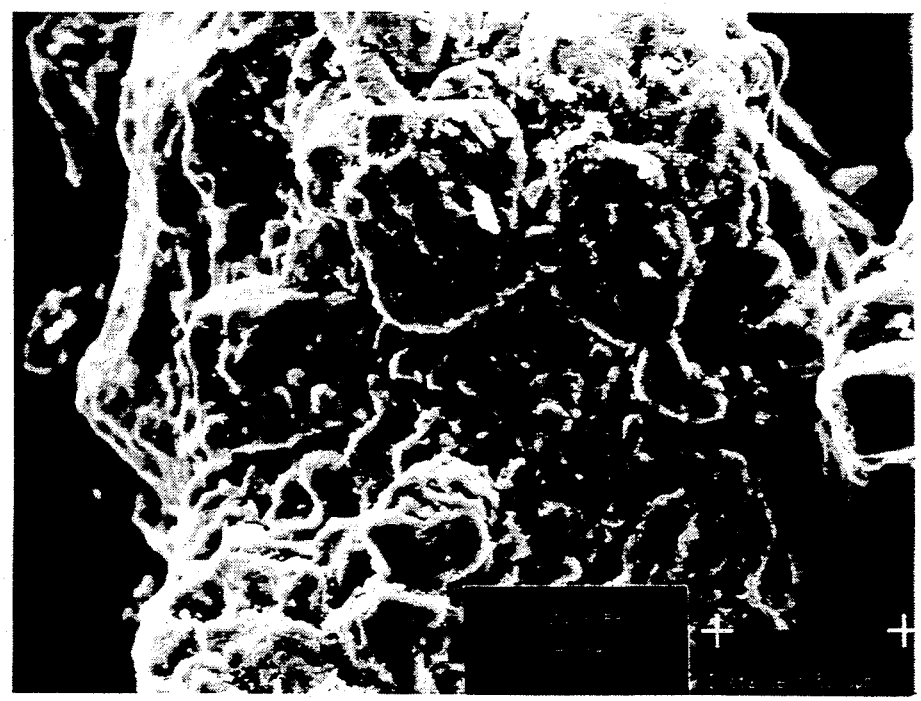
FIG. 1 is a photomicrograph which shows the microcrystals of nifedipine coating the large lactose particles.

In the present invention more than 50% of the particles will have a particle size below the limit stated, preferably more than 60% will be below the limit as stated, more preferably 80% of the particles will be below the stated limit.

In the pharmaceutical compositions of the invention the majority of the microcrystalline particles of nifedipine preferably has a particle size of less than 25 micrometers, more preferably a particle size in the range of from 10 to 25 micrometers.

The pharmaceutically acceptable water soluble diluent may be any diluent which is normally used in the preparation of pharmaceutical compositions, for example lactose, sucrose, mannose, sorbitol, or mixtures thereof. The pharmaceutically acceptable water soluble diluent preferably have a particle size of less than 250 micrometers and preferably also has a specific surface area of greater than 0.5 $m^2$/gram.

The pharmaceutical composition of the invention contains polyvinylpyrrolidone, which is preferably used in an amount of from 20 to 50% by weight based on the weight of nifedipine.

Although polyvinylpyrrrolidone is known as a binder for use in the preparation of various pharmaceutical compositions, in the compositions of the present invention it acts as a retardant in delaying the dissolution of the microcrystalline nifedipine particles.

The present invention also includes within its scope a process for the preparation of the pharmaceutical compositions as defined above, which process comprises dissolving nifedipine and the polyvinylpyrrolidone in a suitable solvent therefore, coating particles of a finely divided pharmaceutically acceptable water soluble diluent which is insoluble in the solvent with the said solution and evaporating the solvent from the surface of the coated diluent particles.

The solvent which is used in the process of the invention must be a solvent for nifedipine and the polyvinylpyrrolidone but should not dissolve the pharmaceutically acceptable diluent. Examples of suitable solvents are chloroform, lower aliphatic alcohols or methylene chloride. The most preferred solvent for use is chloroform.

The solvent evaporates from the surface of the coated diluent particles thus leaving microcrystals of nifedipine, in the presence of the polyvinylpyrrolidone coated onto the particles of the finely divided pharmaceutically acceptable water soluble diluent.

The pharmaceutical composition of the present invention may be formulated into a solid unit dosage form, such as tablets or capsules, in a conventional manner. In the preparation of such formulations conventional additives may be used such as lubricants, binders, stabilizers etc.

The pharmaceutical compositions of the present invention possess a good stability and are easily reproducible. During the preparation of the compositions the microcrystalline nifedipine particles are formed without any milling being required and this prevents the formation of nifedipine dust.

It will be appreciated that dry milling techniques are tedious and expensive and, furthermore, that the dust from a drug such as nifedipine is potentially hazardous. The process of the present invention thus provides an economic and simple route to the production of a pharmaceutical composition comprising nifedipine.

EXAMPLE 1

A batch of 5000 tablets of nifedipine was prepared from the following formulation:

| | |
|---|---|
| Nifedipine | 100 g |
| Polyvinylpyrrolidone | 25 g |
| Chloroform | 500 ml |
| Lactose (surface area 0.52 m$^2$/g) | 1000 g |
| Hydrogenated Vegetable Oil | 11.25 g |
| Talc | 22.50 g |

In this preparation, the nifedipine and polyvinylpyrrolidone were dissolved in the chloroform. The solution was then coated uniformly onto the lactose particles using a high shear mixer and the coated lactose particles were then dried to remove the chloroform solvent therefrom. The coated lactose particles were mixed with the hydrogenated vegetable oil and talc and then formed into tablets by standard tablet manufacturing procedures.

Figure 2:
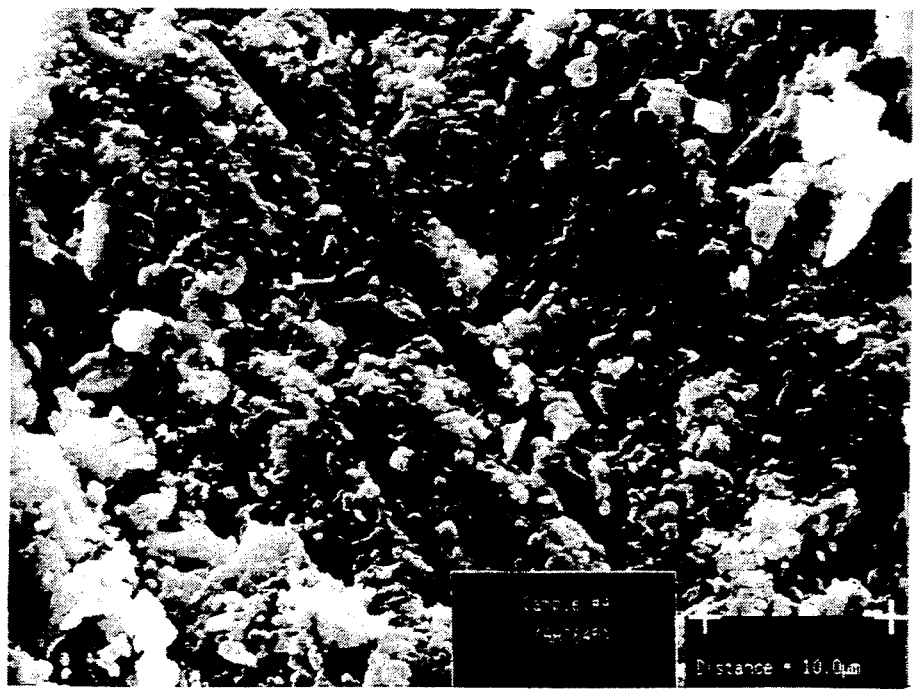
FIG. 2 is a photomicrograph of the same sample taken at a higher magnification.

The coated lactose particles produced by the above process were subjected to scanning electron microscopy. FIG. 1 of the accompanying drawings is a photomicrograph which clearly shows the microcrystals of nifedipine coating the large lactose particles. FIG. 2 is a photomicrograph of the same sample taken at a higher magnification showing the microcrystalline features on the larger crystals more clearly.

The in-vitro dissolution performances of the tablets was measured according to the Paddle Method of U.S. Pharmacopaeia XX at 37° C. and 50 r.p.m. The following results were obtained.

| Time in Hours | Percentage dissolved |
|---|---|
| 1 | 13 |
| 2 | 25 |
| 3 | 36 |
| 4 | 46 |
| 5 | 55 |
| 6 | 64 |
| 7 | 71 |

Figure 3:
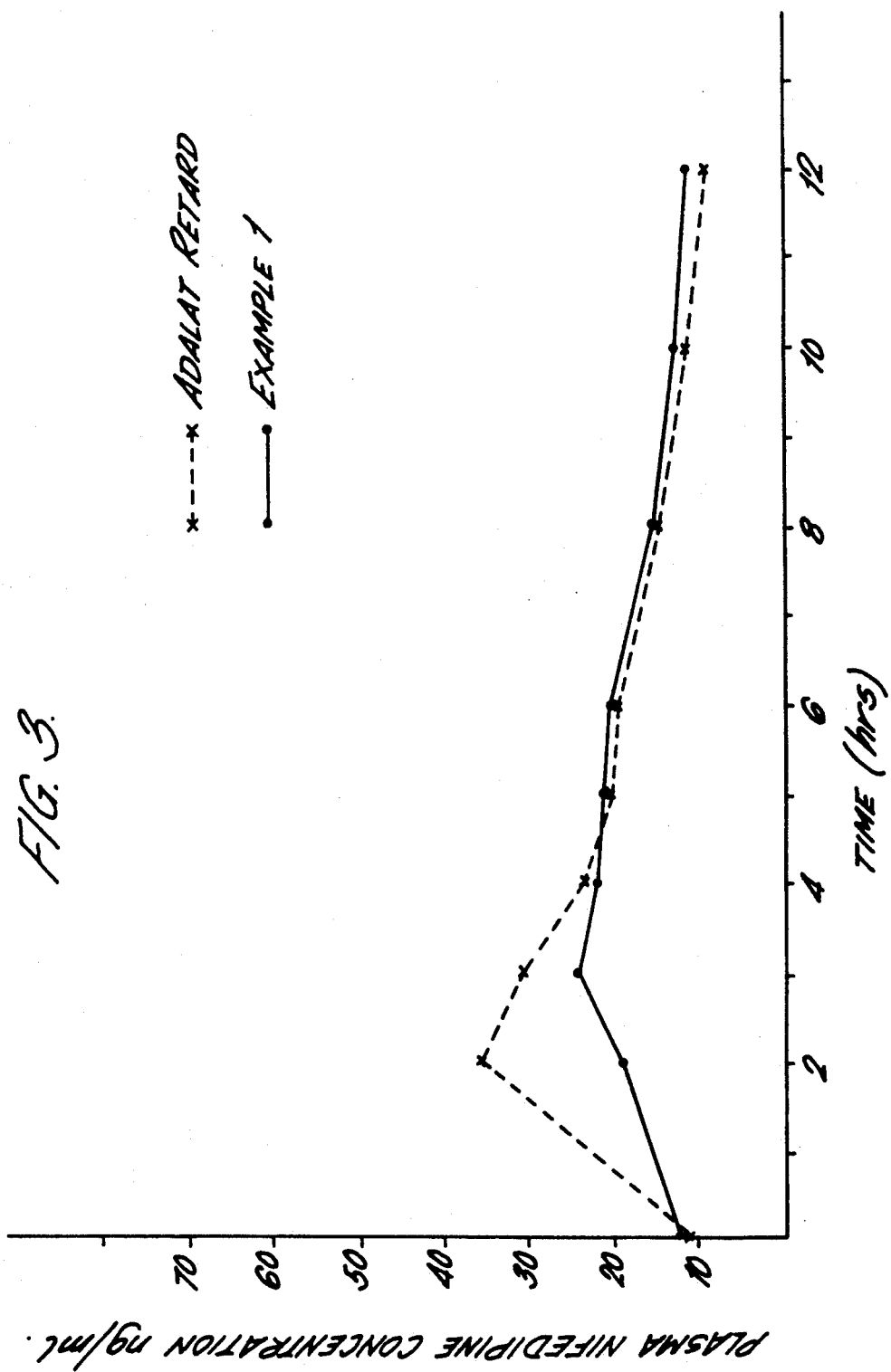
FIG. 3 is a comparison of the steady state plasma nifedipine concentrations following administration of 20 mg of nifedipine twice daily using Adalat Retard or the tablets produced according to Example 1 of the invention.

The tablets produced according to this method were also tested against a nifedipine slow release formulation marketed by Bayer under the Trade Name Adalat Retard. The steady state plasma nifedipine concentrations following administration of 20 mg of nifedipine twice daily using Adalat Retard or the tablets produced according to the present invention are shown in FIG. 3 of the accompanying drawings.

The product of the invention showed a good maintenance of the nifedipine plasma level throughout the twelve hour period and shows more uniform plasma levels than the Adalat Retard composition.

COMPARATIVE EXAMPLE

A batch of 5000 tablets of nifedipine was prepared from the following formulation:

| | |
|---|---|
| Nifedipine | 100 g |
| Chloroform | 500 ml |
| Lactose | 1000 g |
| Hydrogenated Vegetable Oil | 11.25 g |
| Talc | 22.50 g |

The tablets were prepared according to the procedure of Example 1. It will be noted, however, that the polyvinylpyrrolidone was omitted from the above formulation.

The in-vitro dissolution of these tablets was tested according to the procedure detailed in Example 1. The following results were obtained.

| Time in Hours | Percentage Dissolved |
|---|---|
| 1 | 91 |
| 2 | 99 |

Figure 4:
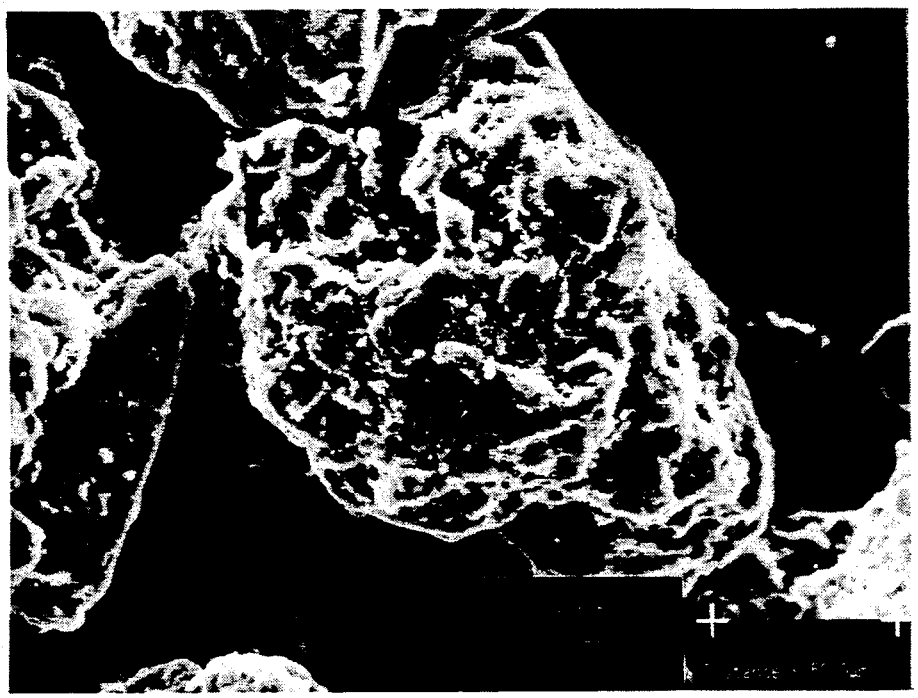
FIG. 4 is a photomicrograph of the tablets of Example 1 of the invention.
Figure 5:
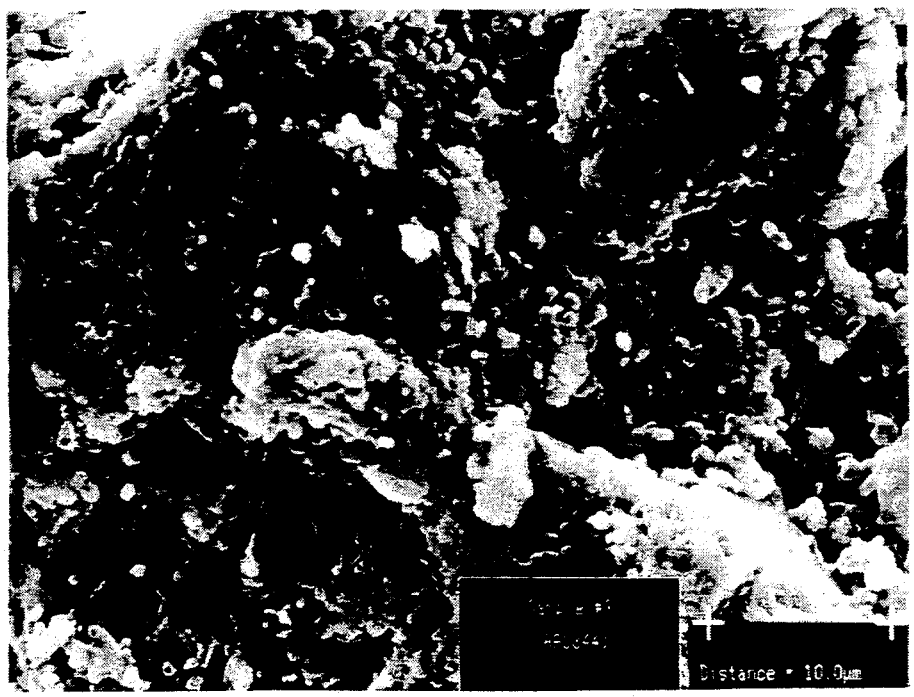
FIG. 5 is an enlargement of FIG. 4.

It can be seen from this rapid dissolution of the tablets that the polyvinylpyrrolidone which is incorporated into the tablets of Example 1 acts as a dissolution rate controlling agent and slows the rate of nifedipine dissolution. FIG. 4 is a photomicrograph of the composition of the above tablets, whilst FIG. 5 is a photomicrograph of the same sample taken at a higher magnification showing the microcrystalline features more clearly. From these photomicrographs it is clear that this product is microcrystalline, despite the absence of polyvinylpyrrolidone from the formulation.

I claim:

1. A pharmaceutical composition which has a decreased dissolution rate of nifedipine and which consists essentially of particles of a pharmaceutically acceptable water soluble diluent coated with microcrystalline particles of nifedipine in the presence of polyvinylpyrrolidone, the majority of the particles of nifedipine having a particle size of at most 100 micrometers and the polyvinylpyrrolidone being present in an amount of from 10 to 90% by weight based on the weight of the nifedipine, wherein the ratio of the polyvinylpyrrolidone to the nifedipine decreases the dissolution rate of nifedipine.

2. Pharmaceutical composition according to claim 1 wherein the majority of the microcrystalline particles of nifedipine have a particle size of less than 25 micrometers.

3. Pharmaceutical composition according to claim 2 wherein the majority of the microcrystalline particles of nifedipine have a particle size in the range of from 10 to 25 micrometers.

4. Pharmaceutical composition according to claim 1 wherein the pharmaceutically acceptable water soluble diluent has a particle size of less than 250 micrometers.

5. Pharmaceutical composition according to claim 1 wherein the pharmaceutically acceptable water soluble diluent is selected from the group consisting of lactose, sucrose, mannose and mixtures thereof.

6. Pharmaceutical composition according to claim 1 wherein the pharmaceutically acceptable diluent has a surface area of greater than 0.5 m$^2$/gram.

7. Pharmaceutical composition according to claim 1 wherein the polyvinylpyrrolidone is used in an amount of from 20 to 50% by weight based on the weight of nifedipine.

8. Pharmaceutical composition according to claim 1 which is in the form of a solid unit dosage form.

9. Pharmaceutical composition according to claim 8 wherein the solid unit dosage form is a tablet or a capsule.

10. Process for the preparation of a pharmaceutical composition according to claim 1, which process consists essentially of:
   (i) dissolving nifedipine and polyvinylpyrrolidone in a suitable solvent therefore, the polyvinylpyrrolidone being used in an amount of from 10 to 90% by weight based on the weight of nifedipine;
   (ii) coating particles of a finely divided pharmaceutically acceptable water soluble diluent which is insoluble in the solvent with the nifedipine/polyvinylpyrrolidone solution; and
   (iii) evaporating the solvent from the surface of the coated diluent particles.

11. Process according to claim 10 wherein the solvent is selected from the group consisting of chloroform, a lower aliphatic alcohol and methylene chloride.

12. Process according to claim 10 wherein the polyvinylpyrrolidone is used in an amount of from 20 to 50% by weight based on the weight of nifedipine.

13. Process according to claim 10 wherein the coated diluent particles are formed into a solid unit dosage form.

14. A pharmaceutical composition according to claim 2 wherein the polyvinylpyrrolidone is used in amount of from 20–50% by weight based on the weight of nifedipine.

15. A pharmaceutical composition according to claim 3 wherein the polyvinylpyrrolidone is used in amount of from 20–50% by weight based on the weight of nifedipine.

16. A pharmaceutical composition according to claim 4 wherein the polyvinylpyrrolidone is used in amount of from 20–50% by weight based on the weight of nifedipine.

17. A pharmaceutical composition according to claim 5 wherein the polyvinylpyrrolidone is used in amount of from 20–50% by weight based on the weight of nifedipine.

18. A pharmaceutical composition according to claim 6 wherein the polyvinylpyrrolidone is used in amount of from 20–50% by weight based on the weight of nifedipine.

* * * * *